US 6,510,342 B1

(12) United States Patent
Park et al.

(10) Patent No.: US 6,510,342 B1
(45) Date of Patent: Jan. 21, 2003

(54) METHODS AND APPARATUS FOR PREVENTING ATRIAL ARRHYTHMIAS BY OVERDRIVE PACING MULTIPLE HEART TISSUE SITES USING AN IMPLANTABLE CARDIAC STIMULATION DEVICE

(75) Inventors: Euljoon Park, Stevenson Ranch, CA (US); Gene A. Bornzin, Simi Valley, CA (US); Joseph J. Florio, La Canada, CA (US); John W. Poore, South Pasadena, CA (US); Douglas T. Kurschinski, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/548,116

(22) Filed: Apr. 12, 2000

(51) Int. Cl.⁷ ................................................ A61N 1/368
(52) U.S. Cl. .......................................... 607/15; 607/14
(58) Field of Search ........................... 607/148, 14, 15, 607/9

(56) References Cited

U.S. PATENT DOCUMENTS

| 4,052,991 A | 10/1977 | Zacouto | 128/419 PG |
| 4,503,857 A | 3/1985 | Boute et al. | 128/419 PG |
| 4,577,633 A * | 3/1986 | Berkovits et al. | 607/10 |

(List continued on next page.)

OTHER PUBLICATIONS

Weintraub, Rogert G., MB, BS, FRACP, et al., "The Congenital Long QT Syndromes in Childhood", JACC, pp: 674–680, vol. 16, No. 3 (Sep. 1990).

Langendorf, R., MD, et al., "Mechanisms of Intermittent Ventricular Bigeminy," Circulation, pp: 422–430, vol. X1 (Mar. 1955).

Moss, Arthur J., MD, et al., "Efficacy of Permanent Pacing in the Management of High–Risk Patients with Long QT Syndrome," Circulation, pp.: 1524–1529, vol. 84, No. 4 (Oct. 1991).

Ohe, Tohru, MD, et al., "The Effects of Cycle Length on the Fragmented Atrial Activity Zone in Patients with Sick Sinus Syndrome", J. Electrocardiology, pp.: 364–368, 20(5) (1987).

Levine, P.A., et al., "Device Management of Paroxysmal Atrial Fibrillation Using the Dynamic Atrial Overdrive Algorithm", pp.: 86–95, Herz–Schrittmacher, 20 (2000).

Fontaine, G., et al., "Value and Limitaitons of the DPG–1 Pacemaker Anti–Arrhythmic Functions", Steinkopff Verlag Pub. Darmstadt (1985) pp.: 224–237.

(List continued on next page.)

Primary Examiner—Kennedy Schaetzle

(57) ABSTRACT

Techniques are described for pacing multiple sites in a patient's heart using overdrive pacing the heart using a pacemaker including techniques where the overdrive pacing rate only increases when at least two intrinsic beats are detected within a determined search period. In one specific technique, an increase in the pacing rate occurs only if two P-waves are detected within X cardiac cycles. In another specific technique, the overdrive pacing rate is increased only if at least two P-waves are detected within a block of N cardiac cycles. In both techniques, the overdrive pacing rate is decreased if no increase has occurred in the last Z cardiac cycles. By increasing the overdrive pacing rate only in response to detection of at least two P-waves within a determined number of cardiac cycles, an excessively high overdrive pacing rate is avoided. Other techniques are described for adaptively adjusting overdrive pacing parameters so as to achieve a determined target degree of pacing of, for example, 95% paced beats. By adaptively adjusting overdrive parameters to maintain a target degree of pacing, the average overdrive pacing rate is minimized while still maintaining a high number of paced beats, thereby reducing the risk of a tachyarrhythmia occurring within the patient.

44 Claims, 8 Drawing Sheets

U.S. PATENT DOCUMENTS

| | | | |
|---|---|---|---|
| 4,809,697 A | | 3/1989 | Causey, III et al. ... 128/419 PT |
| 4,944,299 A | | 7/1990 | Silvian .................. 128/419 PG |
| 4,998,974 A | * | 3/1991 | Aker ........................... 607/14 |
| 5,203,326 A | | 4/1993 | Collins ................... 128/419 G |
| 5,243,978 A | | 9/1993 | Duffin, Jr. ..................... 607/11 |
| 5,403,356 A | | 4/1995 | Hill et al. ..................... 607/14 |
| 5,466,254 A | | 11/1995 | Helland ...................... 607/123 |
| 5,476,483 A | | 12/1995 | Bornzin et al. ............... 607/17 |
| 5,683,429 A | | 11/1997 | Mehra ......................... 602/14 |
| 5,713,929 A | | 2/1998 | Hess et al. .................... 607/14 |
| 5,951,593 A | | 9/1999 | Lu et al. ....................... 607/14 |
| 5,978,709 A | | 11/1999 | Begemann et al. ........... 607/14 |
| 6,058,328 A | | 5/2000 | Levine et al. ................. 607/14 |
| 6,078,836 A | | 6/2000 | Bouhour et al. .............. 607/14 |
| 6,141,586 A | | 10/2000 | Mower .......................... 607/9 |
| 6,161,041 A | | 12/2000 | Stoop et al. ................... 607/14 |
| 6,185,549 B1 | | 2/2001 | Mehra et al. ................. 607/14 |

OTHER PUBLICATIONS

Ragonese, Pietro, et al., "Permanent Overdrive Atrial Pacing in the Chronic Management of Recurrent Postoperative Atrial Reenterant Tachycardia in Patients with Complex Congenital Heart Diseas", PACE, pp.: 2917–2923, vol. 20, Part I (Dec. 1997).

Coumel, Philippe, et al., "Long–Term Prevention of Vagal Atrial Arrhythmias by Atrial Pacing at 90/Minute: Experience with 6 Cases", PACE, pp.:552–560, vol. 6, Part I, (May–Jun. 1983).

Murgatroyd, Francis D., et al., A New Pacing Algorithm for Overdrive Suppression of Atrial Fibrillation:, PACE, vol. 17, Part II, pp.: 1966–1973 (Nov. 1994).

* cited by examiner

METHODS AND APPARATUS FOR PREVENTING ATRIAL ARRHYTHMIAS BY OVERDRIVE PACING MULTIPLE HEART TISSUE SITES USING AN IMPLANTABLE CARDIAC STIMULATION DEVICE

FIELD OF THE INVENTION

The invention generally relates to implantable cardiac stimulation devices such as pacemakers, and in particular, to techniques for overdrive pacing heart tissue to prevent or terminate dysrhythmia.

BACKGROUND OF THE INVENTION

A dysrhythmia is an abnormal heart beat pattern. One example of a dysrhythmia is a bradycardia wherein the heart beats at an abnormally slow rate or where significant pauses occur between consecutive beats. Other examples of dysrhythmias include tachyarrhythmias where the heart beats at an abnormally fast rate, e.g., atrial tachycardia where the atria of the heart beat abnormally fast.

One technique for preventing or terminating dysrhythmias is to overdrive pace the heart where an implantable cardiac stimulation device, such as a pacemaker or implantable cardioverter defibrillator (ICD), applies electrical pacing pulses to the heart at a rate somewhat faster than the intrinsic heart rate of the patient. For bradycardia, the implantable cardiac stimulation device may be programmed to artificially pace the heart at a rate of 60 to 80 pulses per minute (ppm) to thereby prevent the heart from beating too slow and to eliminate any long pauses between heart beats. To prevent tachyarrhythmias from occurring, the implantable cardiac stimulation device artificially paces the heart at a rate of at least five to ten pulses per minute faster than the intrinsic tachyarrhythmia heart rate of the patient. In other words, a slight artificial tachycardia is induced and maintained in an effort to prevent an actual tachycardia from arising.

It is believed that overdrive pacing is effective in at least some patients for preventing or terminating the onset of an actual tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse, has a refractory period subsequent thereto during which time the heart tissue is not responsive to any electrical pulses. A combination of sinus pulses and ectopic pulses can result in a dispersion of the refractory periods which, in turn, can trigger a tachycardia. By overdrive pacing the heart at a uniform rate, the likelihood of the occurrence of ectopic pulses is reduced and the refractory periods within the heart tissue are rendered uniform and periodic. Thus, the dispersion of refractory periods is reduced and tachycardias triggered thereby are substantially avoided.

Thus, it is desirable with patients prone to tachyarrhythmias to ensure that most beats of the heart are paced beats, as any unpaced beats may be ectopic beats. A high percentage of paced beats can be achieved simply by establishing a high overdrive pacing rate. However, a high overdrive pacing rate has disadvantages as well. For example, a high overdrive pacing rate may be unpleasant to the patient, particularly if the artificially-induced heart rate is relatively high in comparison with the heart rate that would otherwise normally occur. A high heart rate may also cause possible damage to the heart or may trigger more serious dysrhythmias, such as a ventricular fibrillation.

A high overdrive pacing rate may be especially problematic in patients suffering from heart failure, particularly if the heart failure is due to an impaired diastolic function. A high overdrive pacing rate may actually exacerbate heart failure in these patients. Also, a high overdrive pacing rate may be a problem in patients with coronary artery disease because increasing the heart rate decreases diastolic time and decreases perfusion, thus intensifying ischemia. Also, the need to apply overdrive pacing pulses operates to deplete the implantable cardiac stimulation device's power supply, perhaps requiring frequent surgical replacement of the power supply. Typically, the power supply is located within the implantable cardiac stimulation device and thus this requires surgical replacement of the implantable cardiac stimulation device.

Problems associated with overdrive pacing are particularly severe for certain aggressive overdrive techniques which trigger an increase in the pacing rate based upon detection of a single intrinsic heart beat. With such techniques, a significant increase in the pacing rate is triggered by detection of a single intrinsic heart beat so as to promptly respond to the occurrence of a high rate tachycardia, such as an SVT. As a result, even in circumstances where a high rate tachycardia has not occurred, detection of a single intrinsic heart beat can cause a significant increase in the overdrive pacing rate, which may be reduced only gradually. If a second intrinsic heart beat is detected before the overdrive pacing rate has been gradually lowered to a standard overdrive pacing rate, a still further increase in the pacing rate occurs. As can be appreciated, the foregoing can cause the overdrive pacing rate to increase significantly, perhaps to 150 ppm or more, even though a high rate tachycardia has not occurred. The aforedescribed problems are addressed by a copending, commonly-assigned patent application to Florio et al., entitled "Methods and Apparatus for Overdrive Pacing Heart Tissue using an Implantable Cardiac Stimulation Device," the contents of which are incorporated herein by reference in their entirety.

An alternative approach to reduce atrial arrhythmias is described in U.S. Pat. No. 5,403,356 to Hill et al. (the Hill patent). The Hill patent describes placing at least two electrodes in the atrium, preferably in the triangle of Koch and/or an area of prolonged effective refractory period elsewhere in the atrium. Pacing pulses are then applied to the multiple electrodes either simultaneously or separated by a short delay.

While each approach offers benefits in avoiding incidences of arrhythmia, e.g., atrial arrhythmia, it is believed that treatment can be further improved by combining selected aspects of both approaches to achieve an improved result. Accordingly, the present invention is directed to that end.

SUMMARY OF THE INVENTION

The present invention is directed toward a method and apparatus for reducing the incidence of atrial arrhythmias by using an overdrive algorithm to determine the application of stimulation pulses to two or more electrodes distributed among multiple sites in a patient's heart, e.g., in the atria. In accordance with a first preferred embodiment, the electrodes may be distributed within a single atrium, e.g., the right atrium, of the patient's heart. Alternatively, a first electrode may be placed in the right atrium and a second electrode may be placed in the coronary sinus or the left atrium or multiple electrodes may be placed proximate to the left atrium.

In accordance with a first aspect of invention, a method is provided for overdrive pacing multiple sites in a patient's heart using an implantable cardiac stimulation device wherein an increase in an overdrive pacing rate is performed only in response to detection of at least two intrinsic beats within a predetermined search period. Initially, an overdrive pacing rate is determined and the heart is paced at the overdrive pacing rate. Intrinsic heart beats arising during overdrive pacing are detected. If at least two intrinsic heart beats are detected within a first predetermined search period, then the overdrive pacing rate is increased by a predetermined rate increment. If at least two intrinsic heart beats are not detected within a second predetermined search period, the overdrive pacing rate is decreased by a predetermined rate of decrements. By increasing the overdrive pacing rate only in response to the detection of at least two intrinsic heart beats within the first predetermined search period, an excessively high heart rate is avoided as might otherwise occur if an overdrive pacing rate increase were based upon detection of only a single intrinsic heart beat.

In an exemplary embodiment, the first predetermined search period extends for X number of cardiac cycles following detection of a first intrinsic beat wherein X is in the range of eight to forty cycles. The second predetermined search period Z is also within the range of eight to forty cardiac cycles. If, after detection of a first intrinsic heart beat, a second heart beat is detected within X cardiac cycles, then the overdrive pacing rate is increased by Y ppm wherein Y is five, ten, fifteen, twenty or twenty-five. If Z cardiac cycles occur without a rate increase, then the rate is decreased by an amount W ppm per cardiac cycle wherein W is one, two, three, four or five.

In a second exemplary embodiment, the first predetermined search period is N consecutive cardiac cycles, wherein N is, for example, ten. Thus, if there are at least two intrinsic heart beats within a set of N consecutive cardiac cycles, the overdrive pacing rate is increased. Otherwise, the overdrive pacing rate is decreased. With the second embodiment, it is easy to program a minimum percentage of paced beats. For example, to attain at least a minimum of 90% paced beats, N is set at ten. If fewer than 90% of the beats are paced beats (i.e., at least two beats out of every ten beats are intrinsic beats), the overdrive pacing rate is increased; otherwise it is decreased. This provides a feedback loop which maintains the pacing rate at a rate sufficient to provide about 90% paced beats on the average.

In still other embodiments, the implantable cardiac stimulation device may periodically suspend overdrive pacing to permit detection of three consecutive intrinsic heart beats. The intrinsic heart rate is calculated based upon those three heart beats and overdrive pacing resumes at a rate corresponding to the intrinsic heart rate. In another embodiment, the implantable cardiac stimulation device periodically determines the intrinsic atrial rate and compares the atrial rate with the current overdrive pacing rate. If the difference between the atrial rate and the overdrive pacing rate exceeds a predetermined threshold amount, the implantable cardiac stimulation device adjusts the overdrive pacing rate to equal the atrial rate. Otherwise, the implantable cardiac stimulation device continues to pace at the current overdrive pacing rate.

In accordance with a second aspect of the invention, a method is provided for adaptively varying overdrive pacing characteristics so as to achieve a predetermined degree of pacing. Overdrive pacing pulses are applied to the heart in accordance with programmed values specifying overdrive pacing characteristics. An actual degree of pacing resulting from the overdrive pacing pulses is determined. The programmed values are then varied based upon the degree of pacing resulting from the overdrive pacing pulses.

In an exemplary embodiment of the second aspect of the invention, overdrive pacing is performed by periodically determining an intrinsic atrial rate, then pacing the heart at a rate equal to the intrinsic rate plus an additional overdrive pacing margin. The overdrive pacing margin is thereafter selectively increased or decreased so as to maintain the actual degree of pacing at about 95% paced beats. To this end, the overdrive pacing margin, which may initially be set to five beats per minute above the intrinsic heart rate, may be incrementally increased or decreased to maintain the percentage of paced beats at the target rate of about 95%.

In a second exemplary embodiment, overdrive pacing is performed in accordance with a dynamic atrial overdrive technique which operates to periodically increase a pacing cycle length (i.e., to decrease the pacing rate) to permit detection of intrinsic paced beats. The pacing cycle length is automatically extended every $N_{MAX}$ cardiac cycles by a predetermined amount. Initially, $N_{MAX}$ may be, for example, ten cycles. In accordance with the invention, the value for $N_{MAX}$ is periodically increased or decreased in accordance with the actual degree of pacing so as to maintain the actual degree of pacing at about 95% paced beats. Hence, possible disadvantages associated with increasing the overdrive pacing rate in response to detection of only a single intrinsic beat are substantially avoided and the average overdrive pacing rate is kept reasonably low. Other programmable values defining the dynamic atrial overdrive algorithm may also be adaptively varied in accordance with the actual degree of pacing.

Hence, with the second aspect of the invention, overdrive pacing characteristics are adaptively varied so as to reduce the average overdrive pacing rate while still maintaining, on the average, the target percentage of paced beats. The degree of risk or discomfort to the patient resulting from overdrive pacing is thereby minimized and the longevity of the power supply of the implantable cardiac stimulation device is increased while still achieving a sufficiently high percentage of paced beats to reduce the risk that a naturally occurring tachyarrhythmia will occur within the patient.

In a significant aspect of the present invention, the aforedescribed overdrive algorithm may be performed via multiple sites in a patient's heart. In a first embodiment, two or more electrodes are distributed in the atria, e.g., the right atrium of the patient's heart, and a combined signal received from the electrodes is used as input to the aforedescribed overdrive algorithm. The algorithm then triggers a single pulse generator that is used to simultaneously drive multiple electrodes to simultaneously stimulate multiple sites in the patient's heart. Alternatively, multiple pulse generators can be used to individually drive the multiple electrodes, thus enabling a programmed time delay between stimulation of each of the sites in the patient's heart. Additionally, cardiac tissue depolarizations can be individually sensed from each of the electrodes and the sensed signal indicating the highest heart rate can be used as input to the overdrive algorithm. Again, pacing pulses can be applied either simultaneously or staggered with a programmed time delay to multiple sites in the patient's heart.

Apparatus embodiments of the invention are also provided. Other aspects, features, and advantages of the invention will be apparent from the detailed description which follows in the combination with the attached drawings.

DETAILED DESCRIPTION OF THE INVENTION

The present invention is directed toward a method and apparatus for reducing the incidence of atrial arrhythmias by using an overdrive algorithm to determine the application of stimulation pulses to two or more electrodes distributed among multiple sites in a patient's heart, e.g., in the atria. In accordance with a first preferred embodiment, the electrodes may be distributed within a single atrium, e.g., the right atrium, of the patient's heart. Alternatively, a first electrode may be placed in the right atrium and a second electrode may be placed in the coronary sinus or the left atrium. Furthermore, the invention relates to techniques for controlling overdrive pacing to the multiple sites so as to achieve and maintain a target degree of pacing and thus suppress tachycardias. The techniques will first be described with reference to FIGS. 1–4 wherein an overdrive pacing rate is increased only in response to detection of at least two intrinsic heart beats within some predetermined number of cardiac cycles. Then, techniques of the invention will be described with reference to FIGS. 5–7 wherein programmable values specifying overdrive pacing characteristics are adaptively varied so as to maintain a target percentage of paced beats.

Figure 1A:
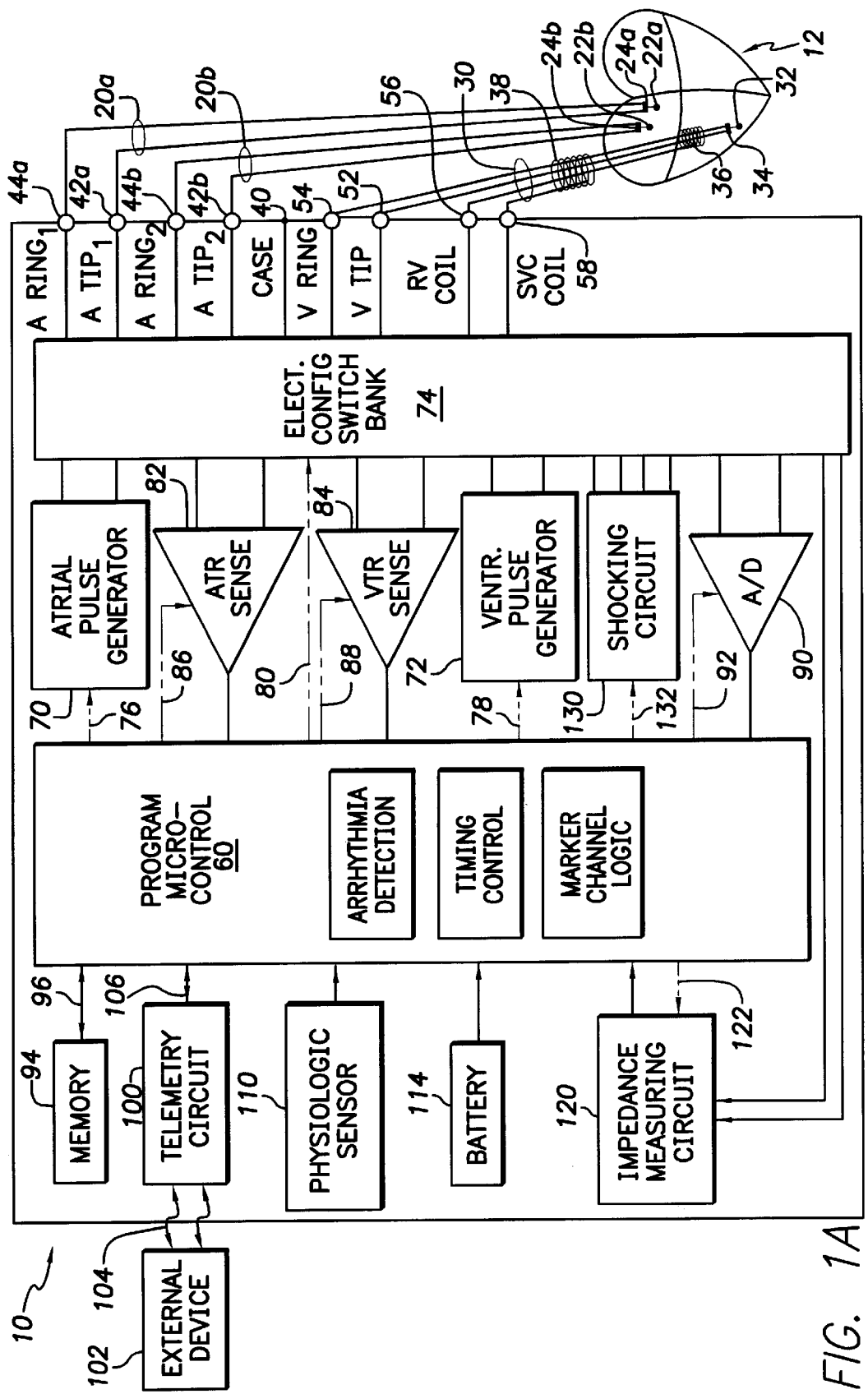
FIG. 1A is a schematic diagram illustrating an implantable cardiac stimulation device, a pacemaker/defibrillator, internally configured in accordance with the invention, and connected to a patient's heart.

In FIG. 1A, a simplified block diagram is shown of a dual-chamber implantable cardiac stimulation device 10 which is capable of treating both fast and slow arrhythmias with stimulation therapy, including cardioversion, defibrillation, and pacing stimulation. While a dual-chamber device is shown, this is for illustration purposes only, one of skill in the art could readily eliminate or disable the appropriate circuitry to provide a single-chamber stimulation device capable of treating one chamber with cardioversion, defibrillation and pacing stimulation or appropriate circuitry may be added to provide a three or four chamber stimulation device.

To provide atrial chamber pacing stimulation and sensing, the implantable cardiac stimulation device 10 is shown in electrical communication with a patient's heart 12 by way of implantable atrial leads 20a and 20b, respectively having atrial tip electrodes 22a and 22b and atrial ring electrodes 24a and 24b. The electrode pairs 22a, 24a and 22b, 24b are preferably distributed among two sites in the right atrium for dual site pacing or one pair is positioned in the right atrium, e.g., in the patient's atrial appendage, and the second pair is positioned in the coronary sinus or the left atrium for bi-atrial pacing. For example, a lead designed for placement in the coronary sinus region could be implanted to deliver left atrial pacing. For a complete description of a coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which patents are hereby incorporated herein by reference. Alternatively, both electrode pairs may be located proximate to the left atrium, i.e., both electrode pairs may located in the left atrium, one electrode pair may be located in the left atrium with the second electrode pair located in the coronary sinus, etc. It is believed that by pacing, either simultaneously or staggered, to multiple (two or more), e.g., atrial, sites in the patient's heart, spontaneous depolarizations of ectopic foci can be suppressed and thus the potential for tachycardia, e.g., atrial tachycardia, can be minimized.

The implantable cardiac stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals and delivering stimulation in the form of pacing and shock therapy to the right ventricle.

The housing 40 (shown schematically) for the implantable cardiac stimulation device 10 includes a connector (not shown) having atrial tip terminals 42a and 42b and atrial ring terminals 44a and 44b, which are adapted for connection to the atrial tip electrodes 22a and 22b and the atrial ring electrodes 24a and 24b, respectively. The housing 40 further includes a ventricular tip terminal 52, a ventricular ring terminal 54, a right ventricular (RV) shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode alone or in combination with one of the coil electrodes, 36 and 38. For convenience, the names of the electrodes are shown next to the terminals.

At the core of the implantable cardiac stimulation device 10 is a programmable microcontroller 60 or other processor which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1A, an atrial pulse generator 70 and a ventricular pulse generator 72 generate pacing stimulation pulses for delivery to the patient's heart by the atrial leads 20a and 20b and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the implantable cardiac stimulation device's timing of such stimulation pulses.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial (ATR) sense amplifier 82 and a ventricular (VTR) sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the implantable cardiac stimulation device 10 to deal effectively with the problem of sensing the low frequency, low amplitude signal characteristics of ventricular fibrillation.

The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 84, as is known in the art.

For arrhythmia detection, the present invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20a, 20b, and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the implantable cardiac stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable cardiac stimulation device 10 may be non-invasively programmed into the memory 94 through a telemetry circuit 100 in telemetric communication with an external device 102, such as a programmer. The telemetry circuit 100 is activated by the microcontroller via control signal 106. The telemetry circuit 100 advantageously allows intracardiac electrograms and status information relating to the operation of the implantable cardiac stimulation device 10 in addition to the data contained in the memory 94 relating to the interaction of the device with the patient's heart to be sent to the external device 102 through an established communication link 104. For examples of such devices, see U.S. Pat. No. 4,809,697, entitled "Interactive Programming and Diagnostic System for use with Implantable Pacemaker" (Causey, III et al.) and U.S. Pat. No. 4,944,299, entitled "High Speed Digital Telemetry System for Implantable Device" (Silvian).

In the preferred embodiment, the implantable cardiac stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV delay at which the atrial and ventricular pulse generators, 70 and 72, generate stimulation pulses. A common type of rate responsive sensor is an activity sensor, such as an accelerometer or a piezoelectric crystal, which is mounted within the housing 40 of the implantable cardiac stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The implantable cardiac stimulation device 10 additionally includes a battery 114 which provides operating power to all of the circuits shown in FIG. 1A. For the implantable cardiac stimulation device 10, which employs shocking therapy, the battery 114 must be capable of operating at low current drains for long periods of time, and, in the case where the pacemaker also performs as a cardioverter/defibrillator, the battery must also be capable of providing high-current pulses (for capacitor charging) when the patient requires a shock pulse. The battery 114 must also have a predictable discharge characteristic so that elective replacement time can be detected. Accordingly, the present invention preferably employs lithium/silver vanadium oxide batteries, as is presently true for many such devices.

The implantable cardiac stimulation device 10 further includes a magnet detection circuitry (not shown) coupled to the microcontroller 60. It is the purpose of the magnet detection circuitry to detect when a magnet is placed over the implantable cardiac stimulation device 10, which magnet may be used by a clinician or patient to perform various functions controlling the implantable cardiac stimulation device 10.

As further shown in FIG. 1A, the present invention preferably includes an impedance measuring circuit 120 which is enabled by the microcontroller 60 by a control signal 122. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that any desired electrode (including the RV and SVC coil electrodes, 36 and 38) may be used. The impedance measuring circuit 120 is not critical to the present invention and is shown for only completeness.

Figure 1B:
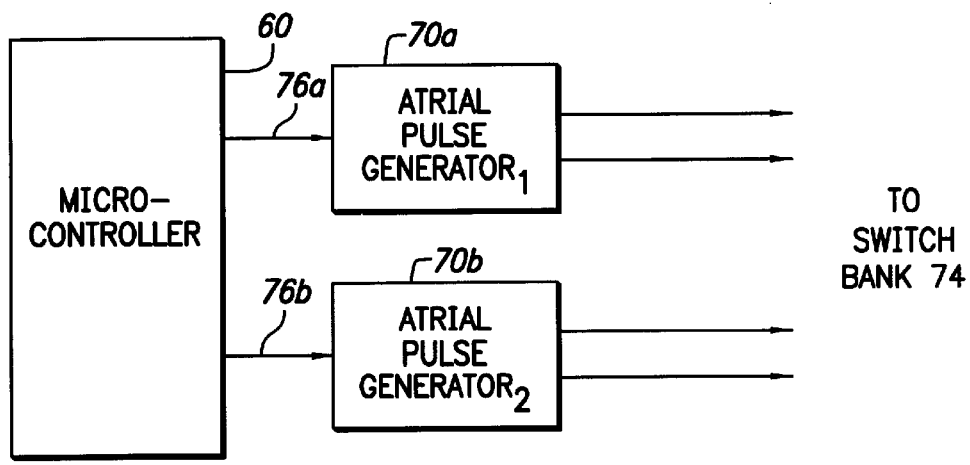
FIG. 1B is a schematic diagram of an alternative embodiment of a portion of the implantable cardiac stimulation device of FIG. 1A showing the use of multiple pulse generators for individually driving each of the implanted electrodes.

FIG. 1B shows a schematic diagram of an alternative embodiment of a portion of the implantable cardiac stimulation device 10 of FIG. 1A showing the use of multiple pulse generators 70a and 70b for individually driving each of the implanted atrial electrode pairs. Each of the pulse generators 70a and 70b are individually controlled by the microcontroller 60 via control signals 76a, 76b. Accordingly, in this embodiment, the pacing of each site can be individually controlled. In operation, this embodiment allows either simultaneous pacing or pacing staggered between the two sites by a determined time delay, e.g., pacing the right atrium in advance of the left atrium.

Figure 1C:
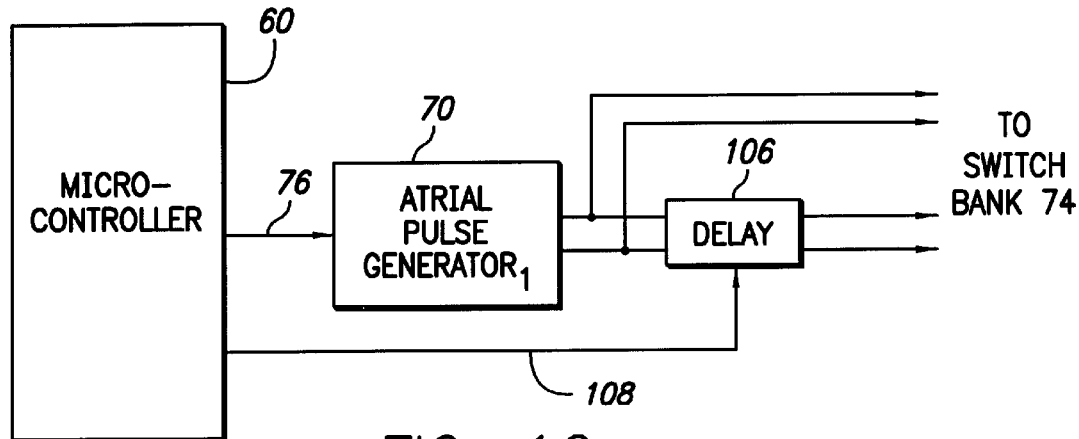
FIG. 1C is a schematic diagram of an alternative embodiment of a portion of the implantable cardiac stimulation device of FIG. 1A showing the use of a pulse delay circuit in conjunction with a pulse generator for individually driving each of the implanted electrodes.

FIG. 1C is a schematic diagram of an alternative embodiment of a portion of the implantable cardiac stimulation device 10 of FIG. 1A showing the use of a pulse delay circuit in conjunction with a pulse generator for individually driving each of the implanted atrial electrodes. This embodiment performs similarly to that described in reference to FIG. 1B except that a single pulse generator 70 is used in conjunction with a pulse delay circuit 106 which is used to stagger the pacing between the multiple sites. Preferably the pulse delay circuit 106 is programmable via control line 108 to enable the microcontroller 60 to alter the stagger amount.

Figure 1D:
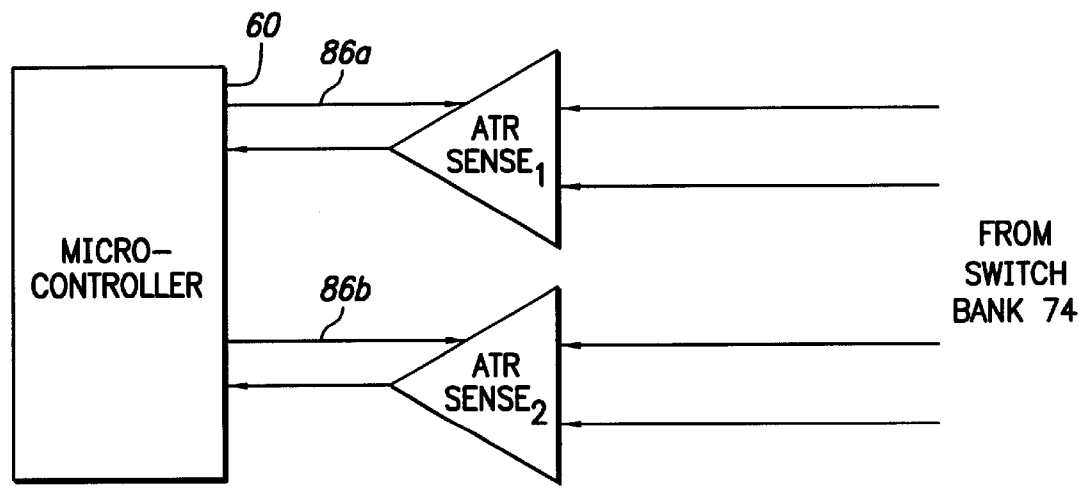
FIG. 1D is a schematic diagram of an alternative embodiment of a portion of the implantable cardiac stimulation device of FIG. 1A showing the use of multiple sense amplifiers for individually sensing depolarizations from the multiple electrodes.

FIG. 1D is a schematic diagram of an alternative embodiment of a portion of the implantable cardiac stimulation device 10 of FIG. 1A showing the use of multiple sense amplifiers 82a and 82b for individually sensing depolarizations from the multiple atrial electrode pairs. Accordingly, in this embodiment, the depolarization rate can be individually sensed at each of the sites in the patient's heart 12. In a first case, the depolarization rate may be the same at each site with a time delay reflecting the conduction speed from the depolarized tissue to each electrode. In a second case, the distribution of ectopic foci may result in a different depolarization rate at each site. In a preferred embodiment, the present invention senses the highest depolarization rate and uses that rate as input to the overdrive algorithm described below. Furthermore, even if the sensed depolarization rates are essentially equivalent, it is preferable that the site at which depolarization is sensed earliest be the site that is stimulated first. For example, if an atrial tachycardia is caused by ectopic foci in the right atrium, an electrode in the right atrium will sense the depolarization before an electrode in the left atrium or coronary sinus. Accordingly, to suppress depolarizations of the ectopic foci, it may be preferable to stimulate right atrial electrode before stimulating the left atrial electrode. Accordingly, the sensing embodiment of FIG. 1D is preferably used in conjunction with the pulse generator embodiment of either FIG. 1B or FIG. 1C to enable this function.

Figure 2:
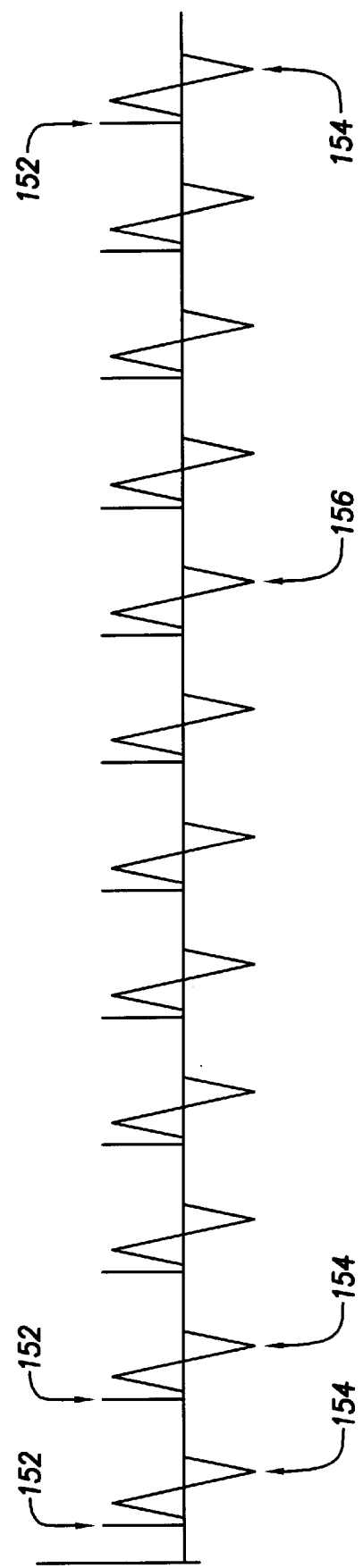
FIG. 2 is a timing diagram illustrating paced beats and unpaced beats within the heart of FIG. 1A.

FIG. 2 illustrates a sequence of pacing pulses 152 administered by the implantable cardiac stimulation device 10 of FIG. 1A. Each electrical pacing pulse triggers an evoked response 154 representative of an artificially induced heart beat. FIG. 2 also illustrates a single unpaced beat 156 not preceded by a pacing pulse 152. Unpaced beat 156 may be, for example, an ectopic beat caused by a naturally occurring electrical signal generated within the heart from a location other than the sinus node from which normal sinus rhythm heart beats are naturally generated. As discussed above, ectopic beats have been found to sometimes trigger tachyarrhythmias and hence it is desirable to minimize the number of ectopic beats. Accordingly, the implantable cardiac stimulation device 10 of FIG. 1A performs an overdrive pacing algorithm intended to generate overdrive pacing pulses 152 at a sufficiently high rate to minimize the number of unpaced beats 156 without causing an unnecessarily high heart rate. To this end, the implantable cardiac stimulation device 10 determines the actual degree of pacing resulting from the overdrive pacing pulses and adaptively modifies the overdrive pacing rate to maintain the actual degree of pacing at about a target degree of pacing wherein about 95% of the total beats are paced beats.

Figure 3:
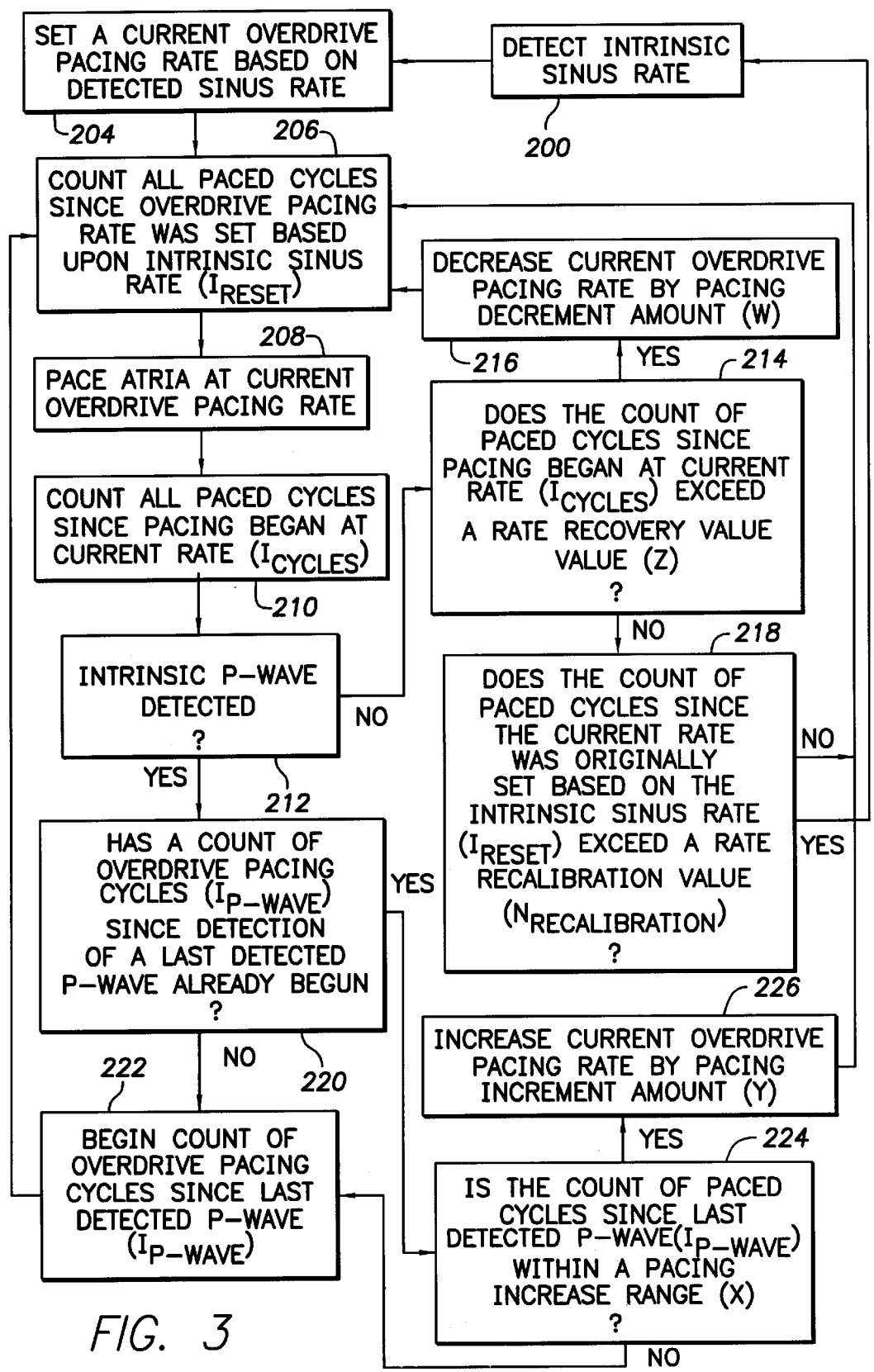
FIG. 3 is a flow chart illustrating an overdrive pacing method wherein an overdrive pacing rate is increased only if at least two intrinsic events are detected within X cardiac cycles of one another.

FIG. 3 illustrates a technique for overdrive pacing a heart wherein an overdrive pacing rate is increased only in response to the detection of at least two intrinsic P-waves occurring within X cardiac cycles of one another wherein X is, typically, between eight and forty cardiac cycles. Briefly, the technique is summarized as follows:

1. Identify a P-wave.
2. If another P-wave occurs within X cardiac cycles, increase the pacing rate by Y bpm.
   a) X is preferably programmable from about 8 to 40 cardiac cycles.
   b) Y is the programmable rate increase and is preferably programmable to 5, 10, 15, 20 or 25 ppm.

3. If Z cardiac cycles occur without a pacing rate increase, then decrease the pacing rate by W ppm.
   a) Z is the dwell time before the pacing rate is decreased and is preferably programmable from 8 to 40 cardiac cycles.
   b) W is preferably programmable at 1, 2, 3, 4, or 5 ppm.

Additionally, the implantable cardiac stimulation device 10 periodically suspends pacing to permit detection of three consecutive P-waves. At that time, the sinus rate is computed based upon the detected P-waves and the overdrive pacing rate is reset to be equal to the sinus rate.

This technique will now be explained more fully with reference to FIG. 3. Initially, at step 200, the intrinsic sinus rate is detected by detecting three consecutive P-waves. At step 204, a current overdrive pacing rate is set to be equal to the detected sinus rate. At step 206, the implantable cardiac stimulation device 10 begins to count the number of paced cycles ($I_{RESET}$) since the overdrive pacing rate was set based upon the intrinsic sinus rate. This count of paced cycles is eventually compared with a rate recalibration value in step 218 (described below) and if it exceeds the recalibration value, step 200 is repeated to detect a new intrinsic sinus rate for resetting of the overdrive pacing rate.

At step 208, the atria of the heart is paced at the current overdrive pacing rate. At step 210, the number of cycles ($I_{CYCLES}$) since pacing began at the current rate is counted. Note that, $I_{RESET}$ and $I_{CYCLES}$ are initially equal to one another. However, as will be described, the values typically diverge from one another with further execution of the method steps. $I_{CYCLES}$ is eventually compared against a rate recovery value Z at step 214 (described below) and if $I_{CYCLES}$ exceeds Z, the overdrive pacing rate is decreased.

At step 212, the implantable cardiac stimulation device 10 detects any intrinsic P-waves. If a P-wave is not detected, processing proceeds to step 214 wherein the count of paced cycles since pacing began at the current rate ($I_{CYCLES}$) is compared with the rate recovery value (Z). If $I_{CYCLES}$ exceeds Z, then step 216 is performed wherein the current overdrive pacing rate is decreased by a pacing decrement amount W, preferably preset to 1, 2, 3, 4, or 5 ppm. Processing then returns to step 206 for continued pacing at the newly reduced overdrive pacing rate. Thus, if at least $I_{CYCLES}$ of pacing occurs before detection of a single intrinsic P-wave, the current overdrive pacing rate is reduced to provide for a rate of recovery. If, at step 214, $I_{CYCLES}$ does not exceed Z, then step 218 is performed wherein the implantable cardiac stimulation device 10 determines whether the count of paced cycles since the current rate was originally set ($I_{RESET}$) exceeds a rate recalibration value ($N_{RECALIBRATION}$). If $I_{RESET}$ exceeds $N_{RECALIBRATION}$, then step 200 is again executed wherein a new sinus rate is detected and the overdrive pacing rate is reset to the new sinus rate. This ensures that the overdrive pacing rate does not remain significantly different from the sinus rate for any extended period of time. If, at step 218, $I_{RESET}$ does not exceed $N_{RECALIBRATION}$, then processing returns to step 206 for additional pacing at the current overdrive pacing rate.

What has been described thus far with respect to FIG. 3 are circumstances wherein no intrinsic P-waves are detected. Steps performed in response to the detection of P-waves will now be described. More specifically, if at step 212 an intrinsic P-wave is detected, then step 220 is performed wherein a determination is made as to whether a count has already begun of the number of overdrive pacing cycles since detection of the last detected P-wave. During the first execution of step 220 following detection of the first P-wave, the count has not yet begun and hence processing continues to step 222 wherein the implantable cardiac stimulation device 10 begins to count the number of overdrive pacing cycles since the last detected P-wave ($I_{P-WAVE}$). Processing then returns to step 206 for additional pacing at the current overdrive pacing rate while incrementing $I_{P-WAVE}$ (along with $I_{RESET}$ and $I_{CYCLES}$) with each additional pacing cycle.

If another P-wave is detected at step 212, then execution proceeds through step 220 to step 224 wherein $I_{P-WAVE}$ is compared with a pacing cycle increment value (X). If $I_{P-WAVE}$ is less than X, indicating that the last two detected intrinsic P-waves are within X cardiac cycles of one another, then step 226 is performed wherein the current overdrive pacing rate is increased by a predetermined pacing increment amount (Y) set to, for example, 5, 10, 15, 20, or 25 ppm. Thereafter, pacing continues from step 206 at the new higher overdrive pacing rate. If, however, at step 224, $I_{P-WAVE}$ was found to be greater than X, meaning that the last two detected intrinsic P-waves were more than X cycles apart, then the overdrive pacing rate is not immediately increased. Instead, processing proceeds to step 222 wherein $I_{P-WAVE}$ is reset to begin a new count of the number of overdrive pacing cycles since the most recently detected P-wave.

Thus, FIG. 3 is a flow chart illustrating one technique for implementing an overdrive pacing algorithm which, among other features, (1) increases an overdrive pacing rate if two P-waves are detected within X cardiac cycles of one another, (2) decreases the overdrive pacing rate if a rate increase does not occur within at least Z cardiac cycles, and (3) resets the overdrive pacing rate to be equal to a detected sinus rate every $N_{RECALIBRATION}$ number of cardiac cycles regardless of the extent to which the overdrive pacing rate is modified during the interim.

Figure 4:
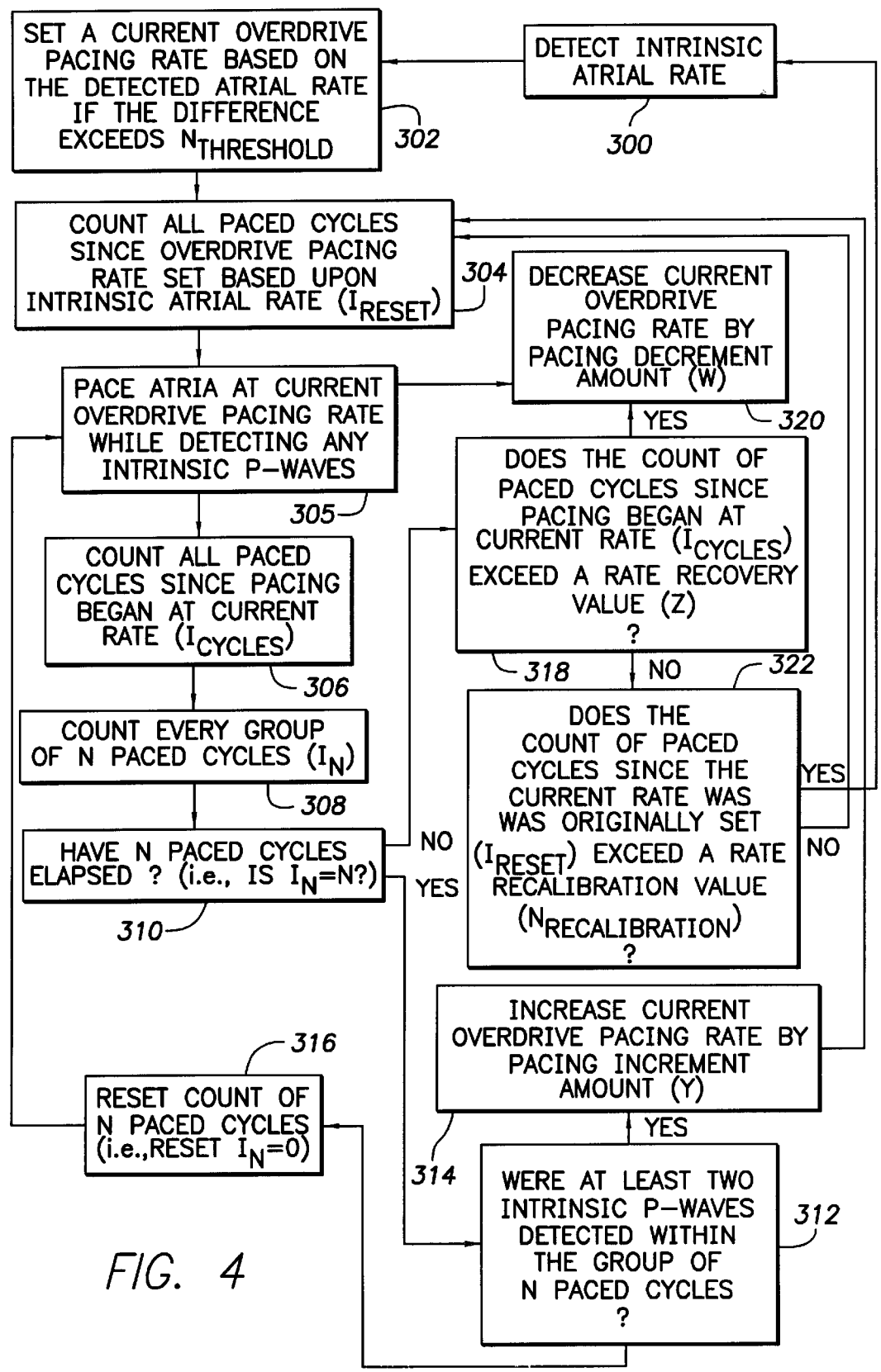
FIG. 4 is a flow chart illustrating an overdrive pacing method wherein an overdrive pacing rate is increased only if at least two intrinsic heart beats are detected within a block of N consecutive cardiac cycles.

FIG. 4 illustrates a method for controlling overdrive pacing wherein an overdrive pacing rate is increased only if at least two intrinsic atrial beats are detected within a block of N consecutive cardiac cycles. The technique of FIG. 4 is summarized as follows:

1. At the conclusion of a block of N cardiac cycles, the implantable cardiac stimulation device determines if there is more than one P-wave in the block of cardiac cycles. If there is more than one P-wave, the pacing rate is increased by Y ppm.
   a) Y is a programmable rate increment and is preferably programmable to 5, 10, 15, 20 or 25 ppm.
2. If Z cardiac cycles occur without increasing the pacing rate, then the pacing rate is decreased by W ppm.
   a) Z is the dwell time before the pacing rate is decreased and is preferably programmable from 8 to 40 cardiac cycles.
   b) W is preferably programmable at 1, 2, 3, 4, or 5 ppm.

Additionally, the implantable cardiac stimulation device 10 periodically suspends pacing to detect the intrinsic atrial rate and compare the intrinsic atrial rate with a current overdrive pacing rate. If the difference between the atrial rate and the overdrive pacing rate exceeds a predetermined threshold ($N_{THRESHOLD}$), then the overdrive pacing rate is reset to the detected atrial rate. Otherwise, overdrive pacing continues at the current pacing rate.

The technique will now be described in greater detail with reference to FIG. 4. Certain steps of FIG. 4 are similar to those of FIG. 3 and, accordingly, will not be re-described in detail. Initially, at steps 300 and 302, the implantable cardiac stimulation device 10 detects the current intrinsic atrial rate and sets a current overdrive pacing rate based on the detected atrial rate. Initially, the overdrive pacing rate is set to be equal to the detected atrial rate. During subsequent iterations of steps 300 and 302, the overdrive pacing rate is set to the atrial rate only if the atrial rate minus the current overdrive pacing rate exceeds $N_{THRESHOLD}$.

At step 304, the implantable cardiac stimulation device 10 begins to count all paced cycles ($I_{RESET}$) since the overdrive pacing rate was set at step 302. At step 305, the implantable cardiac stimulation device 10 paces the atria at the current overdrive pacing rate while detecting any intrinsic P-waves. At step 306, all paced cycles since pacing began at the current rate are detected and counted ($I_{CYCLES}$). At step 308, the implantable cardiac stimulation device 10 also counts every group of N consecutive paced cycles ($I_N$) wherein N is, for example, ten. Initially, the counts initiated at steps 302, 306 and 308 will be the same. As will be seen, however, these counts may diverge from one another with further processing of the method steps.

At step 310, the implantable cardiac stimulation device 10 determines whether N pacing cycles have elapsed by examining $I_N$. If $I_N$ equals N, then step 312 is performed wherein the implantable cardiac stimulation device 10 determines whether at least two intrinsic P-waves have been detected within the group of N paced cycles. If so, the current overdrive pacing rate is increased at step 314 by an amount Y wherein Y is equal to, for example, 5, 10, 15, 20 or 25 ppm. Thereafter, processing returns to step 304 for additional atrial pacing at the new overdrive pacing rate. If, at step 312, at least two intrinsic P-waves were not detected within the group of N paced cycles, then step 316 is performed wherein the count of N paced cycles ($I_N$) is reset such that the next set of N consecutive paced cycles may be counted. In this manner, the overdrive pacing rate is increased if, and only if, at least two P-waves are detected within a group of N consecutive cardiac cycles.

If, at step 310, N paced cycles have not yet elapsed (i.e., the count $I_N$ is less than N), then step 318 is performed wherein the implantable cardiac stimulation device 10 determines whether the count of paced cycles since pacing began at the current rate ($I_{PACED}$) exceeds a rate recovery value (Z). If so, then at step 320, the overdrive pacing rate is decreased by a pacing decrement amount W, wherein W is preset to, for example, 1, 2, 3, 4 or 5 ppm. Hence, if the overdrive pacing rate has not been increased as a result of the detection of at least two P-waves within a block of N cycles, then the overdrive pacing rate is decreased to provide rate recovery.

If, at step 318, $I_{CYCLES}$ does not exceed Z, then step 322 is performed wherein the implantable cardiac stimulation device 10 determines whether the count of paced cycles since the current rate originally set ($I_{RESET}$) in step 302 exceeds a rate calibration value $N_{RECALIBRATION}$. If so, then steps 300 and 302 are repeated wherein overdrive pacing is suspended to permit detection of the intrinsic atrial rate and the overdrive pacing rate is then set based upon the intrinsic atrial rate. As noted above, within step 302, a determination is made as to whether the difference between the intrinsic atrial rate and the overdrive pacing rate exceeds a threshold $N_{THRESHOLD}$ and, if not, the overdrive pacing rate is not reset to be equal to the atrial rate. If, at step 322, $I_{RESET}$ does not exceed $N_{RECALIBRATION}$, then processing merely returns to step 304 for additional pacing at the current overdrive pacing rate.

Thus, FIG. 4 illustrates an overdrive pacing technique wherein, among other features, (1) an overdrive pacing rate is increased only if at least two P-waves are detected within a block of N consecutive cardiac cycles, (2) the overdrive pacing rate is decreased if the overdrive pacing rate is not increased within Z consecutive cardiac cycles, and (3) the overdrive pacing rate is periodically reset to an intrinsic atrial rate if the difference between the atrial rate and the current overdrive pacing rate exceeds a predetermined threshold. By increasing the overdrive pacing rate only in response to the detection of at least two P-waves within a block of N consecutive cardiac cycles, excessively aggressive overdrive pacing rate increases are avoided. Additionally, with appropriate selection of N, a minimum percentage of paced cycles can be achieved on the average. For example, by setting N equal to ten, the average percentage of paced cycles will be maintained at about 90%. If more than ten percent of the cardiac cycles are intrinsic cycles, then the overdrive pacing rate is increased. Otherwise, the overdrive pacing rate is periodically decreased. Hence, an average of about 90% is sustained.

Figure 5:
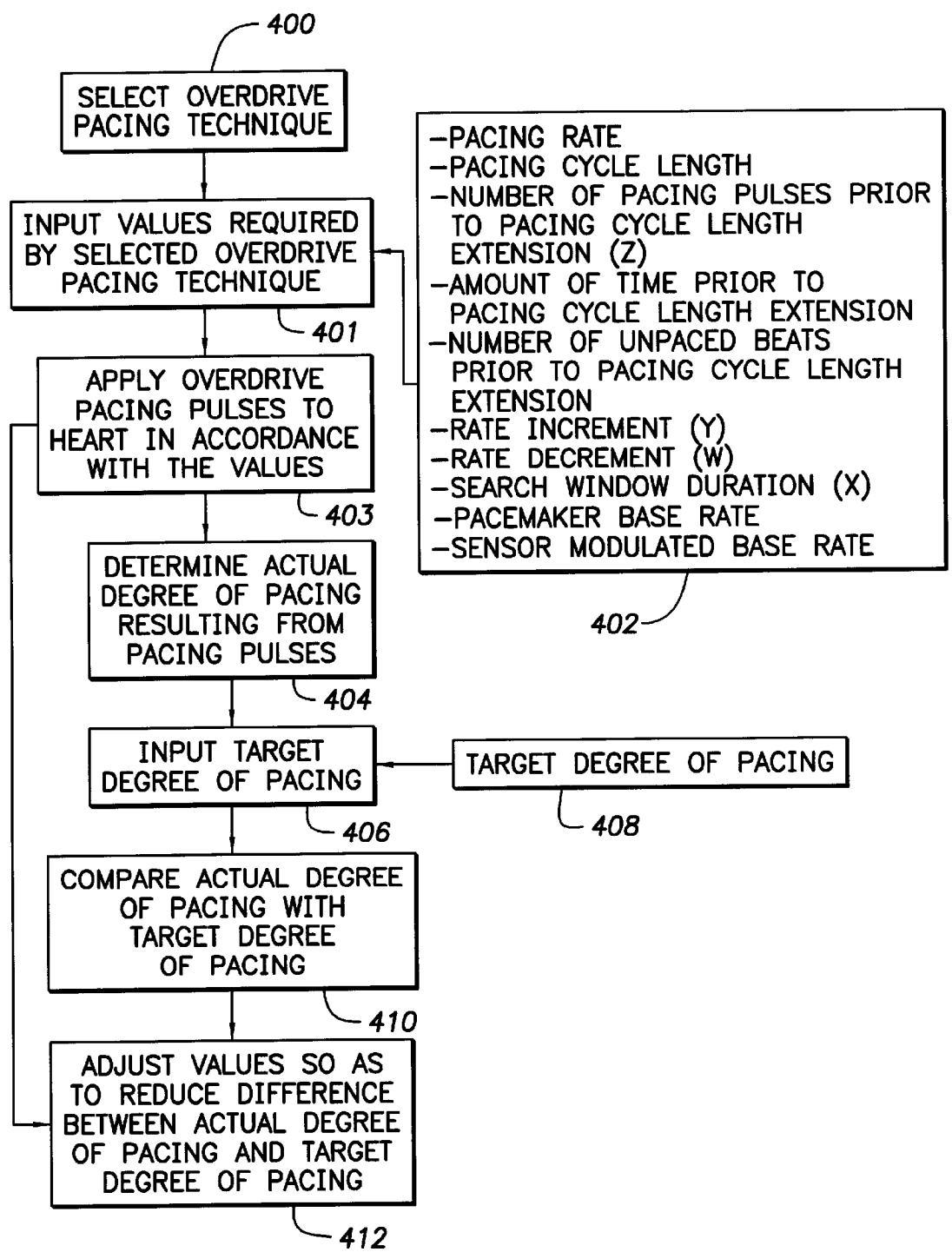
FIG. 5 is a flow chart illustrating a method for adaptively varying programmable values defining overdrive pacing characteristics so as to maintain a target degree of pacing.

With reference to FIG. 5, techniques for adaptively varying overdrive pacing characteristics are summarized. Initially, at step 400, a particular overdrive pacing technique or algorithm is selected by the implantable cardiac stimulation device 10. Then, at step 401, programmable values, ie., control values, are input from a memory 402 for control of the operation of the algorithm. (If the implantable cardiac stimulation device 10 is capable of performing only a single overdrive pacing technique, step 400 is not necessary.) Depending upon the overdrive pacing technique, the programmable values may be representative of: an overdrive pacing rate, an overdrive pacing margin, a pacing cycle length, a number of pacing pulses prior to pacing cycle length extension (Z), an amount of time prior to pacing cycle length extension, a number of unpaced beats prior to pacing cycle length extension, a rate increment magnitude (Y), a rate decrement magnitude (W), a search window duration (X), a pacemaker base rate, and a sensor modulated base rate.

At step 403, the implantable cardiac stimulation device 10 applies overdrive pacing pulses to the heart in accordance with the requisite programmable values. While overdrive pacing is performed, the implantable cardiac stimulation device 10 performs steps 404–412 to adjust the programmable values so as to reduce any difference between an actual degree of pacing and a target degree of pacing. More specifically, at step 404, the implantable cardiac stimulation device 10 determines the actual degree of pacing resulting from the pacing pulses. The actual degree of pacing may be represented by a percentage of paced beats (determined as a function of time or as a function of cardiac cycles) or by any other appropriate factor. At step 406, a target degree of pacing is input from a memory 408 and, at step 410, the implantable cardiac stimulation device 10 compares the actual degree of pacing with the target degree of pacing. At step 412, the implantable cardiac stimulation device 10 adjusts the values used from memory 402 so as to reduce any difference between the actual degree of pacing and the target degree of pacing. The specific adjustment depends upon a particular programmable value being adjusted. In some cases, a value may need to be increased so as to cause a decrease in the degree of pacing. In other cases, a value may need to be decreased so as to cause a decrease in the degree of pacing. The direction of the adjustment and the magnitude of the adjustment are set so as to achieve a negative feedback loop which converges the actual degree of pacing to the target degree of pacing. To this end, routine experiments are performed to determine optimal values for adjusting the various parameters to achieve the desired feedback loop and to eliminate adjustment values, if any, which may result in a positive feedback loop causing the actual degree of pacing to deviate from the target degree of pacing, rather than to converge to the target degree of pacing. The resulting adjustment in the values may be linear or nonlinear, depending upon the particular programmable values and depending upon the amount of difference, if any, between the actual degree of pacing and the target degree of pacing. As can be appreciated, a wide range of possible adjustments can be employed consistent with the invention depending upon the characteristics of the overdrive pacing technique being implemented. In many cases, two or more programmable values are adjusted simultaneously. For example, both the overdrive pacing margin and the number of pacing pulses prior to a pacing cycle length extension may be adaptively adjusted.

A first specific example of the technique of FIG. 5 will now be described with reference to FIG. 6. In this specific example, the implantable cardiac stimulation device 10 operates to maintain the overdrive pacing rate at a rate equal to the intrinsic rate plus a programmable rate margin. The rate margin is adaptively varied so as to maintain a target degree of pacing. Initially, at step 500, the implantable cardiac stimulation device 10 inputs an initial overdrive pacing margin from a memory unit 502. The margin may be, for example, five beats per minute (bpm)—indicating that the heart is to be paced at a rate equal to the intrinsic heart rate plus five bpm. At step 504, the implantable cardiac stimulation device 10 periodically determines the intrinsic heart rate and administers overdrive pacing pulses to the heart at a rate equal to the intrinsic rate plus the overdrive pacing margin. For example, if the intrinsic rate is found to be 60 bpm, the implantable cardiac stimulation device 10 overdrive paces the heart at a rate of 65 ppm. If the intrinsic rate is found to increase to 80 bpm, then the overdrive pacing rate automatically increases to 85 ppm. In this manner, the implantable cardiac stimulation device 10 seeks to maintain the overdrive pacing rate at a rate slightly higher than the intrinsic rate at all times.

A determination of the intrinsic rate at step 504 may be performed, for example, by periodically deactivating overdrive pacing, thereby permitting detection of intrinsic beats from which the intrinsic heart rate is determined. In this regard, an estimate of the intrinsic heart rate may be calculated based upon the time between the detected intrinsic beats. The greater the number of intrinsic beats that are detected, the more precise the determination of the intrinsic heart rate.

Step 506 is periodically performed wherein the implantable cardiac stimulation device 10 counts the number of paced beats and the number of unpaced beats until a predetermined period of time, such as 60 seconds, has elapsed. Alternatively, the implantable cardiac stimulation device 10 counts the beats until a predetermined number of total beats, such as 100 beats, have been counted. The implantable cardiac stimulation device 10 then calculates a percentage of the number of paced beats out of a total number of beats. In the example of FIG. 2, with nine paced beats and one unpaced beat, the percentage of paced beats is about 90%. At step 508, the implantable cardiac stimulation device 10 inputs a target degree of pacing from a memory unit 510. The target of pacing may be, for example, 95% paced beats. At step 512, the implantable cardiac stimulation device 10 determines whether the actual percentage of paced beats determined at step 506 is greater than the target percentage of paced beats input at step 508. If so, then step 514 is performed wherein the implantable cardiac stimulation device 10 automatically decreases the overdrive pacing margin by a predetermined amount, such as one ppm. If not, then step 516 is performed wherein the implantable cardiac stimulation device 10 automatically increases the overdrive pacing margin by the predetermined amount.

Thereafter, step 504 is performed using the adjusted overdrive pacing margin. Hence overdrive pacing may now occur at a rate of six ppm above the intrinsic rate or perhaps only at a rate of fourppm above the intrinsic rate. With repeated iterations of steps 504–516, the degree of overdrive pacing is thereby periodically, adaptively adjusted so as to maintain the actual percentage of paced beats at an amount about equal to the target degree of pacing, e.g., at about 95%. Hence, if the initial overdrive pacing adjustment factor was too high such that substantially 100% of heart beats were paced beats, the overdrive pacing adjustment factor is decreased somewhat to permit occasional detection of an unpaced beat. This helps ensure that the overdrive pacing rate is not so high so as to possibly adversely affect the health of the patient. Also, avoidance of an unnecessarily high overdrive pacing rate helps preserve battery longevity. Moreover, in embodiments wherein the implantable cardiac stimulation device 10 relies upon detection of an occasional intrinsic beat so as to determine the intrinsic heart rate, a reduction of the overdrive pacing rate helps ensure that intrinsic beats are occasionally detected. On the other hand, if the actual degree of overdrive pacing was found to be significantly less than 95%, then the overdrive pacing rate is increased so as to prevent too many intrinsic beats from occurring which might trigger a tachyarrhythmia.

Figure 6:
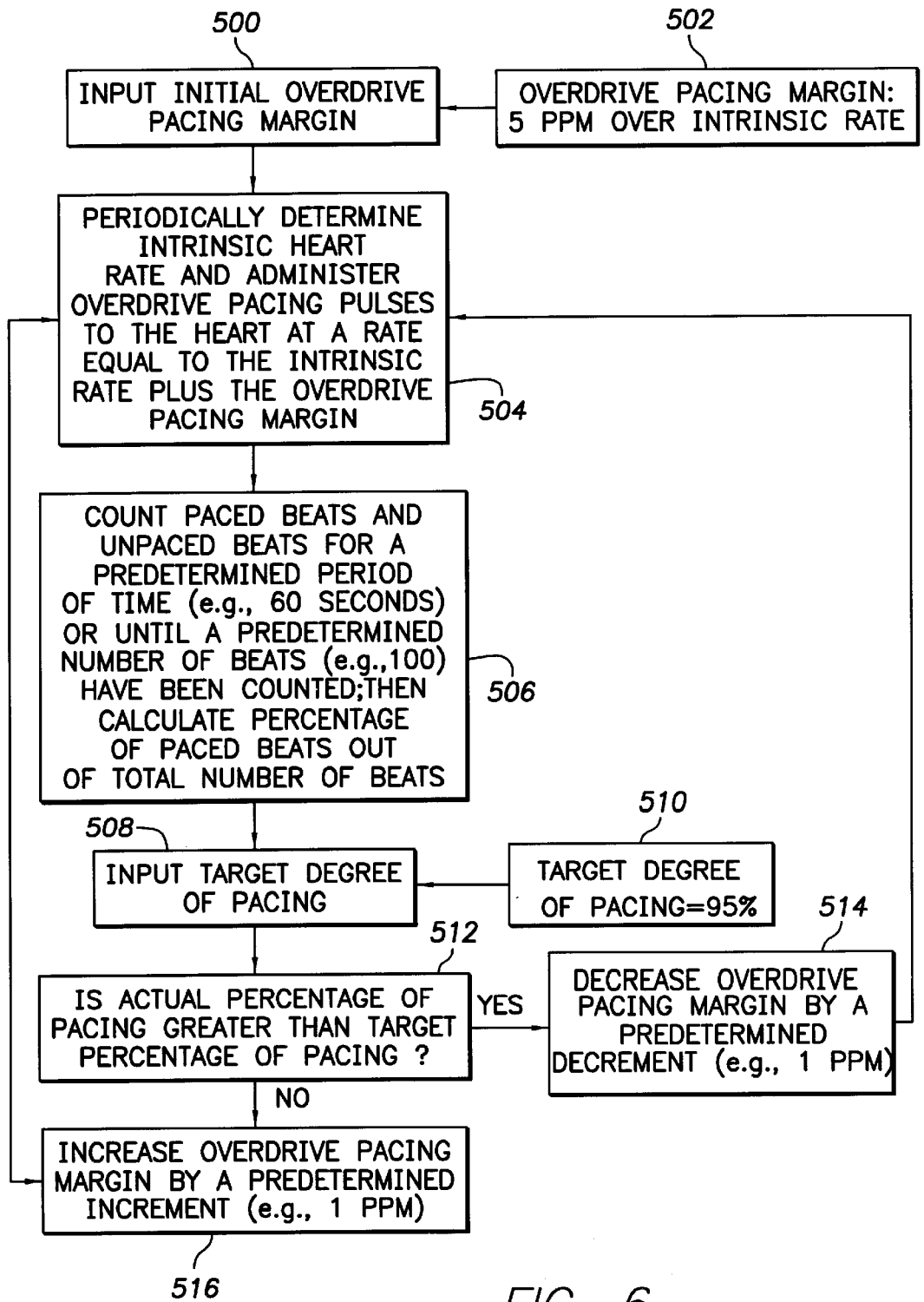
FIG. 6 is a flow chart of the method of FIG. 5 configured for adaptively varying an overdrive pacing rate.

Although not specifically shown in FIG. 6, if, at step 512, the actual percentage of pacing is found to be exactly equal to the target degree of pacing, then the implantable cardiac stimulation device 10 may be configured to not adjust the overdrive pacing adjustment factor either up or down. Also, the predetermined amount by which the overdrive pacing margin is increased may differ from that in which it is decreased. Also, the predetermined amounts may vary depending upon the current overdrive pacing rate or upon the current overdrive pacing adjustment factor. For example, if the overdrive pacing margin is currently set to 20 ppm, the factor may be increased or decreased by a greater amount than if the overdrive pacing margin was currently set to two or three ppm. Likewise, if the current overdrive pacing rate (i.e., the sum of the current intrinsic heart rate and the current overdrive pacing margin) is particularly high, then the predetermined amounts may also be relatively high. Also, note that the overdrive pacing margin may, at times, be negative. As can be appreciated, a wide range of alternatives may be provided consistent with the principles of the invention.

Another specific example of the technique of FIG. 5 will now be described with reference to FIG. 7. In this specific example, the implantable cardiac stimulation device 10 performs a dynamic atrial overdrive technique wherein detection of a single P-wave triggers an immediate, significant increase in the overdrive pacing rate and wherein, after an increase, the pacing cycle length is periodically extended to gradually reduce the overdrive pacing rate. More specifically, the dynamic atrial overdrive technique operates as follows. The implantable cardiac stimulation device 10 monitors the atria of the heart and detects P-waves and, in response to detection of a single P-wave, increases the overdrive pacing rate by a programmable increment value which depends upon whether the current overdrive base rate is within: 1) a lower rate overdrive (LRO) regime of between 25 and 59 ppm, 2) a middle rate overdrive regime (MRO) of between 60 and 149 ppm, or 3) an upper rate overdrive (URO) of between 150 and 185 ppm.

Within the LRO regime, the implantable cardiac stimulation device 10 increases the overdrive pacing rate with each sensed P-wave by an LRO increment programmable value, e.g., 5, 10, 15, 20 and 25 ppm. Within the URO regime, the implantable cardiac stimulation device 10 increases the overdrive pacing rate with each sensed P-wave by a URO increment programmable value, e.g., 5 or 10 ppm. (Typically, the LRO increment value is programmed to a high value, such as 25 ppm, whereas the URO increment is programmed to a low value such as 5 ppm.) Within the MRO regime, the implantable cardiac stimulation device 10 increases the overdrive pacing rate with each sensed P-wave by an MRO increment which is a blended value between the LRO increment and the URO increment. The MRO increment is equal to the LRO increment when the base rate is 60 ppm. The MRO increment varies gradually when the base rate is in the range of 60 ppm to 150 ppm until the increment is equal to the URO increment when the base rate is equal to 150 ppm.

The implantable cardiac stimulation device 10 also exploits a dynamic rate recovery technique wherein the overdrive base rate is decreased if a predetermined number of pacing cycles occur without any detected P-waves. The predetermined number of cycles and the amount of the decrease are both programmable. The amount of the decrease varies depending upon whether the base overdrive pacing rate is within one of two regimes.

The specific operation of the implantable cardiac stimulation device 10 within the various regimes is described with reference to the following examples.

As an example of operation within the LRO regime, if the current overdrive pacing rate is 45 ppm, the LRO increment value is 5 ppm, and a P-wave is sensed, the current overdrive pacing rate is immediately increased to 50 ppm. If the P-wave arises from intrinsic atrial activity occurring at a rate of 53 bpm, then a second P-wave will be detected before a paced beat can be generated (because the overdrive base rate is still below the intrinsic rate). Hence, another P-wave is detected and the overdrive pacing rate increases to 55 ppm.

As another example of operation within the LRO regime, if the current overdrive pacing rate is 55 ppm, the LRO increment is 25 ppm, the URO increment is 5 ppm, and the patient experiences an SVT at 160 bpm, then the overdrive pacing rate increases by 25 ppm with each sensed atrial beat until the overdrive pacing rate exceeds 60 ppm. Then, any further increments begin at slightly less than the LRO increment of 25 ppm and are gradually reduced to the URO increment of 5 ppm when the overdrive pacing rate exceeds 150 ppm.

To provide rate recovery, the implantable cardiac stimulation device 10 counts the number of pacing pulses delivered at a current overdrive pacing rate and, if the number of cycles exceeds a threshold value $N_{MAX}$, the implantable cardiac stimulation device 10 decreases the overdrive pacing rate by increasing a pacing cycle length (CL) equal to the amount of time between individual pacing pulses. $N_{MAX}$ is preferably programmable within a range of 1 to 32 cycles. Thus, if $N_{MAX}$ is programmed to 10 cycles and the overdrive pacing rate has remained constant for 10 cycles, then the CL is increased by a programmable rate recovery value. In this manner, so long as no intrinsic activity is detected, the overdrive pacing rate gradually decreases. Whenever intrinsic atrial activity is sensed, the counter associated with $N_{MAX}$ is reset and, in accordance with the techniques already described, the overdrive pacing rate is incremented. Exemplary programmable CL increment values are:

Milliseconds/Cycle
  6;13
  6;19
  13;19
  19;25

As noted, an increase in the pacing cycle length causes a corresponding decrease in the overdrive pacing rate. In the foregoing, the first value represents the increase in CL in milliseconds per cycle to be used if the current base rate is over 100 ppm. The second value represents the increase in CL in milliseconds per cycle to be used if the current base rate is 100 ppm or less. Thus, two base CL increment regimes are used.

In a specific rate recovery example, if the current overdrive pacing rate is 102 ppm, the intrinsic atrial rate is 90 ppm, and the dynamic rate recovery values are programmed to 6;19 milliseconds/cycle, then the pacing cycle length decreases after every $N_{MAX}$ as follows:

(1) 595 milliseconds (101 ppm)
(2) 601 milliseconds (100 ppm)
(3) 620 milliseconds (97 ppm)
(4) 639 milliseconds (94 ppm)
(5) 658 milliseconds (91 ppm)

Thus, the implantable cardiac stimulation device 10 employs a dynamic atrial overdrive technique which increases an overdrive base rate very promptly in response to detection of intrinsic atrial activity (i.e., P-waves) and provides a rate recovery technique for reducing the overdrive pacing rate when overdrive pacing is no longer needed. The degree of increment or decrement to the overdrive pacing base rate depends, as described above, upon the current base rate regime. Additional variations to the overdrive pacing rate may be based upon detection of premature atrial contractions (PACs) or other intrinsic events.

Figure 7:
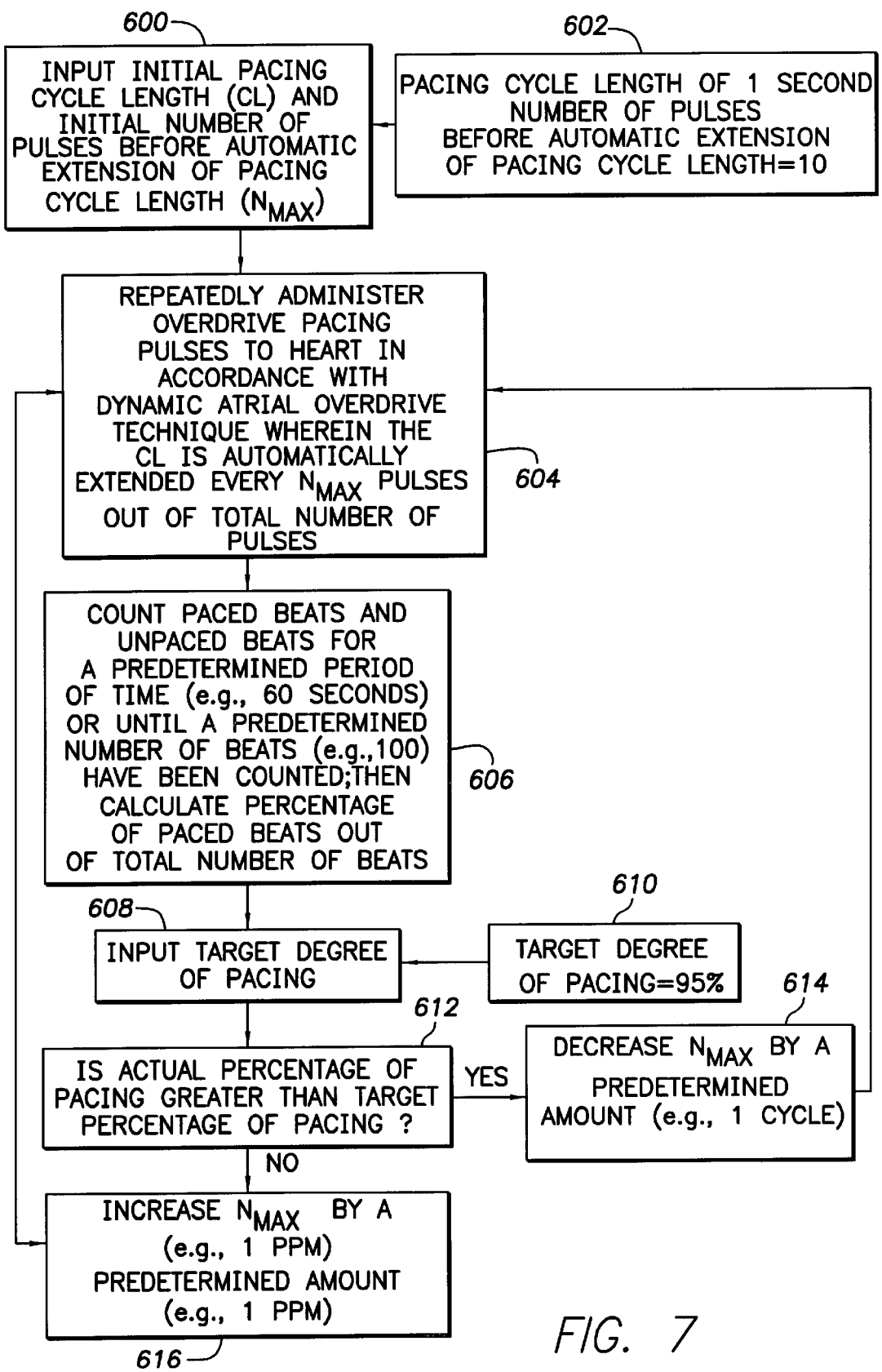
FIG. 7 is a flow chart illustrating a method for adaptively modifying the automatic pacing cycle length adjustment to maintain a target degree of pacing.

In the technique of FIG. 7, $N_{MAX}$ is adaptively varied to maintain a target degree of pacing. Initially, at step 600, the implantable cardiac stimulation device 10 inputs both an initial pacing cycle length (CL) and $N_{MAX}$ from a memory unit 602. CL may be, for example, one second (corresponding to an overdrive pacing rate of 60 ppm) and $N_{MAX}$ may be, for example, initially set to ten.

At step 604, the implantable cardiac stimulation device 10 repeatedly administers overdrive pacing pulses to the heart in accordance with the dynamic atrial overdrive algorithm described above wherein the CL is automatically extended every $N_{MAX}$ pulses to allow occasional detection of intrinsic heart beats or other intrinsic activity. While step 604 is performed, the implantable cardiac stimulation device 10 additionally performs steps 606–616 as follows. The implantable cardiac stimulation device 10 counts the number of paced beats and unpaced beats for either a predetermined period of time or a predetermined number of pulses and then calculates the percentage of paced beats at step 606. A target degree of pacing is input at step 608 from a memory 610 and, at step 612, the implantable cardiac stimulation device 10 determines whether the actual percentage of pacing is greater than the target percentage of pacing. If so, then $N_{MAX}$ is decreased by a predetermined amount, such as one cycle, at step 614. If not, then $N_{MAX}$ is increased by a predetermined amount, such as one cycle, at step 616. Thereafter, the overdrive pacing performed by the implantable cardiac stimulation device 10 during step 604 is performed using the adjusted value for $N_{MAX}$. With repeated iterations of steps 604–616, the actual degree of pacing is maintained substantially at or near the target degree of pacing so as to prevent excessive overdrive pacing while still minimizing the number of non-paced beats. In this regard, $N_{MAX}$ is decreased when the actual percentage of pacing is greater than the target percentage of pacing so as to permit a more prompt detection of an intrinsic pulse from which a new intrinsic heart rate is determined. By permitting a more prompt detection of a next intrinsic beat, the overdrive pacing rate can thereby be adjusted in accordance with the dynamic atrial overdrive algorithm to more closely match the intrinsic rate. In contrast, by increasing $N_{MAX}$ if the actual percentage of pacing is found to be less than 95%, a greater amount of time elapses prior to detection of a next intrinsic pulse, thereby delaying readjustment of the overdrive pacing rate. This may result in a generally higher overdrive pacing rate. In any case, regardless of whether the adjustments to $N_{MAX}$ result in an increase or decrease in the overall average overdrive pacing rate, the adjustments to $N_{MAX}$ will typically operate to maintain the percentage of paced beats at about the target percentage and the advantages set forth above are achieved.

In another specific example of the technique of FIG. 5, the implantable cardiac stimulation device 10 employs a technique for modulating the base rate of the implantable cardiac stimulation device 10 based upon circadian rhythms of the patient. The technique for modulating the base rate is described in U.S. Pat. No. 5,476,483 to Bornzin et al. which is incorporated by reference herein. Briefly, in accordance with the technique of the Bomzin et al. patent, the base rate associated with a transfer function of a rate-responsive cardiac pacemaker is modulated. Activity sensor measurements are used to derive activity variance measurements, which in turn are used to modulate the base pacing rate. In one embodiment, a histogram is used to store activity variance measurements collected over a period of about one week. A histogram is used to derive an activity variance threshold, which is compared to current activity variance measurements to determine if the patient is asleep. If the patient is deemed to be asleep, the pacing rate is set to a rate that comfortably meets the low metabolic demands of the patient during sleep. In alternative embodiments, the activity variance measurements are applied to a base rate slope to modulate the base pacing rate.

Thus, the base rate can be modulated and as such, the percentage of time that underlying, intrinsic P-waves are detectable during a search period can be adjusted by adaptively adjusting the base rate in accordance with the adaptive techniques described above. With proper selection of appropriate adaptive adjustment values (when the implantable cardiac stimulation device extends an atrial escape interval to permit detection of an underlying, intrinsic P-wave), the adjusted base rate will limit the extension of the escape interval so that the base rate is in fact higher than the underlying atrial rate. Accordingly, there will be few, if any, emerging P-waves. More specifically, parameters sleep_rate and BPR_slope within Equation 9 of the Bomzin et al. patent are adaptively adjusted so as to achieve a target degree of pacing. Increasing sleep_rate and BPR_slope has the effect of increasing the base rate and thus increasing the percentage of atrial pacing.

What has been described are various techniques for pacing multiple sites in a patient's heart using overdrive pacing including techniques for adaptively adjusting overdrive pacing programmable values so as to maintain a desired or target degree of overdrive pacing, or to maintain any other desirable characteristic of the overdrive pacing. The overdrive pacing techniques have been described primarily with reference to flow charts illustrating steps performed by components of an implantable cardiac stimulating device. Each method step of the flow charts additionally represents a functional component for performing the method step. The functional component may comprise individual hardware devices or may comprise software components. In some cases a single functional component will perform two or more method steps. In other cases two or more functional components in combination will perform a single method step. In general, the techniques described herein may be implemented using any appropriate technology such as hardware, software, firmware, or the like.

The examples described herein are merely illustrative of the invention and should not be construed as limiting the scope of the invention. Accordingly, the scope of the present invention is defined by the following claims.

What is claimed is:

1. A method for controlling overdrive pacing of a patient's heart using an implantable cardiac stimulation device connected to a plurality of electrodes implanted in a patient's heart, the method comprising the steps of:

sensing intrinsic atrial depolarizations of the patient's heart via the plurality of electrodes;

determining an overdrive pacing rate according to the sensed atrial depolarizations; and overdrive pacing the heart via the plurality of electrodes at the overdrive pacing rate, wherein the overdrive pacing step sequentially supplies stimulation pulses to the electrodes implanted in the patient's heart.

2. The method of claim 1 wherein the plurality of electrodes are implanted in the atria of the patient's heart.

3. The method of claim 1 wherein the plurality of electrodes are implanted in the right atrium of the patient's heart.

4. The method of claim 1 wherein the plurality of electrodes are implanted proximate to the left atrium of the patient's heart.

5. The method of claim 1 wherein a first electrode is implanted in the right atrium of the patient's heart and a second electrode is implanted in the coronary sinus of the patient's heart.

6. The method of claim 1 wherein a first electrode is implanted in the right atrium of the patient's heart and a second electrode is implanted in left atrium of the patient's heart.

7. The method of claim 1 wherein the sensing step individually senses depolarizations from the plurality of electrodes and the determining step determines the overdrive pacing rate according to the highest sensed depolarization rate.

8. The method of claim 1 further comprising the steps of:

detecting intrinsic heart beats via the plurality of electrodes arising during the overdrive pacing;

increasing the overdrive pacing rate by a determined rate increment if at least two intrinsic heart beats are detected within a first determined search period; and decreasing the overdrive pacing rate by a determined rate decrement if at least two intrinsic heart beats are not detected within a second determined search period.

9. The method of claim 8 wherein the first determined search period extends for a first determined number of overdrive paced cycles.

10. The method of claim 9 wherein the first determined search period begins with a first detected intrinsic beat.

11. The method of claim 9 wherein the first determined search period is between 8 and 40 cycles, inclusive.

12. The method of claim 9 wherein the first determined search period begins with a first paced beat.

13. The method of claim 12 wherein the first determined search period is 10 cycles.

14. The method of claim 8 wherein the second determined search period begins following an increase in the overdrive pacing rate.

15. The method of claim 14 wherein the second determined search period is between 8 and 40 cycles, inclusive.

16. The method of claim 8 wherein the determined rate increment is selected from a group including 5, 10, 15, 20, and 25 ppm.

17. The method of claim 8 wherein the determined rate decrement is selected from a group including 1, 2, 3, 4, and 5 ppm.

18. The method of claim 1 wherein the step of determining the overdrive pacing rate includes the steps of:
   determining an atrial rate according to depolarizations sensed from the plurality of electrodes; and
   setting the overdrive pacing rate to be equal to the atrial rate.

19. The method of claim 18 further including the steps of:
   periodically determining an updated atrial rate;
   comparing the updated atrial rate with a current overdrive pacing rate; and
   resetting the overdrive pacing rate to be equal to the updated atrial rate if the updated atrial rate exceeds the current overdrive pacing rate by a determined amount.

20. A method of controlling overdrive pacing of a patient's heart using an implantable cardiac stimulation device connected to a plurality of electrodes implanted in a patient's heart, the method comprising the steps of:
   sensing intrinsic atrial depolarizations of the patient's heart via the plurality of electrodes;
   determining an overdrive pacing rate according to the sensed atrial depolarizations; and
   overdrive pacing the heart via the plurality of electrodes at the overdrive pacing rate, wherein the step of determining the overdrive pacing rate includes the steps of (a) determining a sinus rate; and (b) setting the overdrive pacing rate to be equal to the sinus rate.

21. The method of claim 20 wherein the step of determining the sinus rate includes the steps of:
   detecting at least three consecutive sinus P-waves;
   determining an average interval between the P-waves; and
   calculating the sinus rate based upon the average interval.

22. The method of claim 20 further including the step of periodically re-determining the overdrive pacing rate by:
   suspending overdrive pacing;
   detecting at least three consecutive P-waves while overdrive pacing is suspended;
   determining an updated sinus rate based upon the at least three consecutive P-waves; and
   setting the overdrive pacing rate based upon the updated sinus rate.

23. An implantable cardiac stimulation device configured for overdrive pacing a patient's heart via a plurality of electrodes implanted in a patient's heart, the device comprising:
   at least one sensing circuit for sensing intrinsic atrial depolarizations of the patient's heart via the plurality of electrodes;
   a processor for determining an overdrive pacing rate according to the sensed atrial depolarizations; and
   a first and a second pulse generator for sequentially supplying stimulation pulses to the electrodes implanted in the patient's heart for overdrive pacing the heart via the plurality of electrodes at the overdrive pacing rate determined by the processor.

24. The device of claim 23 wherein the plurality of electrodes are adapted to be implanted in the atria of the patient's heart.

25. The device of claim 23 wherein the plurality of electrodes are adapted to be implanted in the right atrium of the patient's heart.

26. The device of claim 23 wherein the plurality of electrodes are implanted proximate to the left atrium of the patient's heart.

27. The device of claim 23 wherein a first electrode is implanted in the right atrium of the patient's heart and a second electrode is implanted in the coronary sinus of the patient's heart.

28. The device of claim 23 wherein a first electrode is implanted in the right atrium of the patient's heart and a second electrode is implanted in left atrium of the patient's heart.

29. The device of claim 23 wherein:
   the at least one sensing circuit comprises a first and second sensing circuit for individually sensing depolarizations from the plurality of electrodes; and wherein
   the processor determines the overdrive pacing rate according the highest sensed depolarization rate.

30. The device of claim 23 wherein the processor includes:
   means for detecting intrinsic heart beats via the plurality of electrodes arising during the overdrive pacing;
   means for increasing the overdrive pacing rate by a determined rate increment if at least two intrinsic heart beats are detected within a first determined search period; and
   means for decreasing the overdrive pacing rate by a determined rate decrement if at least two intrinsic heart beats are not detected within a second determined search period.

31. The device of claim 30 wherein the first determined search period extends for a first determined number of overdrive paced cycles.

32. The device of claim 31 wherein the first determined search period begins with a first detected intrinsic beat.

33. The device of claim 30 wherein the first determined search period is between 8 and 40 cycles, inclusive.

34. The device of claim 30 wherein the first determined search period begins with a first paced beat.

35. The device of claim 34 wherein the first determined search period is 10 cycles.

36. The device of claim 30 wherein the second determined search period begins following an increase in the overdrive pacing rate.

37. The device of claim 36 wherein the second determined search period is between 8 and 40 cycles, inclusive.

38. The device of claim 30 wherein the determined rate increment is selected from a group including 5, 10, 15, 20, and 25 ppm.

39. The device of claim 30 wherein the determined rate decrement is selected from a group including 1, 2, 3, 4, and 5 ppm.

40. The device of claim 23 wherein the processor additionally comprises:
   means for determining a sinus rate; and
   means for setting the overdrive pacing rate to be equal to the sinus rate.

41. The device of claim 40 wherein the processor additionally comprises:
   means for detecting at least three consecutive sinus P-waves;
   means for determining an average interval between the P-waves; and
   means for calculating the sinus rate based upon the average interval.

42. The device of claim 40 wherein the processor periodically redetermines the overdrive pacing rate, the processor additionally comprising:

means for suspending overdrive pacing;

means for detecting at least three consecutive P-waves while overdrive pacing is suspended;

means for determining an updated sinus rate based upon the at least three consecutive P-waves; and means for setting the overdrive pacing rate based upon the updated sinus rate.

43. The device of claim 23 wherein the processor additionally comprises:

means for determining an atrial rate according to depolarizations sensed from the plurality of electrodes; and means for setting the overdrive pacing rate to be equal to the atrial rate.

44. The device of claim 43 wherein the processor additionally comprises:

means for periodically determining an updated atrial rate;

means for comparing the updated atrial rate with a current overdrive pacing rate; and means for resetting the overdrive pacing rate to be equal to the updated atrial rate if the updated atrial rate exceeds the current overdrive pacing rate by a determined amount.

\* \* \* \* \*